United States Patent
Yoshizaki et al.

(10) Patent No.: US 9,421,515 B2
(45) Date of Patent: Aug. 23, 2016

(54) POROUS CARBON MATERIAL, ADSORBENT, ORAL ADSORBENT, MEDICAL ADSORBENT, FILLER FOR BLOOD PURIFICATION COLUMN, WATER PURIFICATION ADSORBENT, CLEANSING AGENT, CARRIER, SUSTAINED RELEASE PHARMACEUTICAL, CELL CULTURE SCAFFOLD, MASK, CARBON/POLYMER COMPOSITE, ADSORBENT SHEET AND FUNCTIONAL FOOD

(75) Inventors: Makoto Yoshizaki, Kanagawa (JP); Hironori Iida, Kanagawa (JP); Takashi Obikawa, Kanagawa (JP); Shinichiro Yamada, Kanagawa (JP); Seiichiro Tabata, Kanagawa (JP); Kazuma Usami, Kanagawa (JP); Masakazu Mitsugi, Kanagawa (JP); Hirotsugu Ishihara, Tokyo (JP); Shun Yamanoi, Kanagawa (JP); Machiko Minatoya, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/006,187

(22) PCT Filed: Mar. 7, 2012

(86) PCT No.: PCT/JP2012/001565
§ 371 (c)(1),
(2), (4) Date: Sep. 19, 2013

(87) PCT Pub. No.: WO2012/132251
PCT Pub. Date: Oct. 4, 2012

(65) Prior Publication Data
US 2014/0011666 A1 Jan. 9, 2014

(30) Foreign Application Priority Data
Mar. 31, 2011 (JP) ................. 2011-077354

(51) Int. Cl.
*B01J 10/00* (2006.01)
*B01J 20/28* (2006.01)
(Continued)

(52) U.S. Cl.
CPC ............ *B01J 20/28085* (2013.01); *A23L 1/30* (2013.01); *A23L 1/304* (2013.01); *A24D 3/163* (2013.01);
(Continued)

(58) Field of Classification Search
CPC ............ A23L 1/30; A24D 3/16; A61K 33/44; A61K 47/04; B01J 20/20; C12M 3/00; C01B 31/08–31/14
USPC .................................................. 502/416–417
See application file for complete search history.

(56) References Cited

U.S. PATENT DOCUMENTS 7,832,412 B2 * 11/2010 Xue et al. ..................... 131/334
2008/0047313 A1 * 2/2008 Johnson et al. ................... 71/31
(Continued)

FOREIGN PATENT DOCUMENTS

JP 52-123990 10/1997
JP 11-217207 8/1999
(Continued)

OTHER PUBLICATIONS

"Peat definition". The Free Dictionary. <http://www.thefreedictionary.com/peat> Accessed Oct. 31, 2013.*
Ojeda, M. L., et al. "On comparing BJH and NLDFT pore-size distributions determined from N2 sorption on SBA-15 substrata". DOI: 10.1039/B300821E (Paper) Phys. Chem. Chem. Phys., 2003, 5, 1859-1866.*
(Continued)

*Primary Examiner* — Richard M Rump
(74) *Attorney, Agent, or Firm* — Chip Law Group

(57) ABSTRACT

[Object] To provide a porous carbon material that is able to adsorb desired substances efficiently.
[Solving Means] A porous carbon material of the present invention uses peat as a raw material, and has a total of volumes of fine pores having a diameter of from $1 \times 10^{-8}$ m to $2 \times 10^{-7}$ m, obtained by non-localized density functional theory method, of 0.5 cm$^3$/g or more, or has a volume of fine pores obtained by BHJ method of 0.5 cm$^3$/g or more.

20 Claims, 4 Drawing Sheets

(51) Int. Cl.

| | | |
|---|---|---|
| A23L 1/304 | (2006.01) | |
| A24D 3/16 | (2006.01) | |
| A61K 9/14 | (2006.01) | |
| A61K 9/70 | (2006.01) | |
| A61K 33/44 | (2006.01) | |
| A23L 1/30 | (2006.01) | |
| A41D 13/11 | (2006.01) | |
| C02F 1/28 | (2006.01) | |
| C12M 1/12 | (2006.01) | |
| C01B 31/08 | (2006.01) | |
| C01B 31/10 | (2006.01) | |
| B01J 20/20 | (2006.01) | |
| B01J 20/30 | (2006.01) | |

(52) U.S. Cl.
CPC ............... *A41D 13/11* (2013.01); *A61K 9/143* (2013.01); *A61K 9/70* (2013.01); *A61K 33/44* (2013.01); *B01J 20/20* (2013.01); *B01J 20/28035* (2013.01); *B01J 20/28064* (2013.01); *B01J 20/28069* (2013.01); *B01J 20/28078* (2013.01); *B01J 20/28083* (2013.01); *B01J 20/3078* (2013.01); *B01J 20/3085* (2013.01); *C01B 31/081* (2013.01); *C01B 31/10* (2013.01); *C02F 1/281* (2013.01); *C02F 1/283* (2013.01); *C12M 25/14* (2013.01); *B01J 2220/485* (2013.01); *C02F 1/288* (2013.01)

(56) References Cited

U.S. PATENT DOCUMENTS

| | | | |
|---|---|---|---|
| 2010/0069507 A1* | 3/2010 | Tabata et al. | 514/769 |
| 2010/0291167 A1 | 11/2010 | Iida et al. | |
| 2011/0135561 A1* | 6/2011 | Tabata et al. | 423/445 R |
| 2011/0223494 A1* | 9/2011 | Feaver et al. | 429/405 |
| 2011/0244012 A1 | 10/2011 | Iida et al. | |

FOREIGN PATENT DOCUMENTS

| | | |
|---|---|---|
| JP | 2004-182511 | 7/2004 |
| JP | 2004-345921 | 9/2004 |
| JP | 9007-043171 | 2/2007 |
| JP | 2007-054833 | 3/2007 |
| JP | 2008-273816 | 11/2008 |
| JP | 2010-104979 | 5/2010 |
| JP | 2010-106007 | 5/2010 |
| WO | WO 2010013785 A1 * | 2/2010 |

OTHER PUBLICATIONS

Donald, Jaclyn, Yasuo Ohtsuka, and Chunbao Charles Xu. "Effects of activation agents and intrinsic minerals on pore development in activated carbons derived from a Canadian peat." Materials Letters 65.4 (2011): 744-747.*

Donald et al., Effects of activation agents and intrinsic minerals on pore development in activated carbons derived from a Canadian peat. Materials Letters. Feb. 28, 2011;65(4):744-7.

* cited by examiner (A)

Main portion (B)

Nonwoven fabric
Porous carbon material sheet
Nonwoven fabric

POROUS CARBON MATERIAL, ADSORBENT, ORAL ADSORBENT, MEDICAL ADSORBENT, FILLER FOR BLOOD PURIFICATION COLUMN, WATER PURIFICATION ADSORBENT, CLEANSING AGENT, CARRIER, SUSTAINED RELEASE PHARMACEUTICAL, CELL CULTURE SCAFFOLD, MASK, CARBON/POLYMER COMPOSITE, ADSORBENT SHEET AND FUNCTIONAL FOOD

CROSS-REFERENCES TO RELATED APPLICATIONS

The present application is the National Stage of International Application No. PCT/JP2012/001565, filed in the Japanese Patent Office as a Receiving Office on Mar. 7, 2012, titled "POROUS CARBON MATERIAL, ADSORBENT, ORALLY ADMINISTRABLE ADSORBENT, ADSORBENT FOR MEDICAL USE, FILLER FOR BLOOD PURIFICATION COLUMN, ADSORBENT FOR WATER PURIFICATION, CLEANSING AGENT, CARRIER, AGENT FOR EXTENDED RELEASE OF DRUGS, CELL CULTURE SCAFFOLD MATERIAL, MASK, CARBON/POLYMER COMPOSITE, ADSORPTIVE SHEET, AND FUNCTIONAL FOOD" which claims the priority benefit to Japanese Patent Application No. 2011-077354, filed in the Japanese Patent Office on Mar. 31, 2011, titled "POROUS CARBON MATERIAL, ADSORBENT, ORALLY ADMINISTRABLE ADSORBENT, ADSORBENT FOR MEDICAL USE, FILLER FOR BLOOD PURIFICATION COLUMN, ADSORBENT FOR WATER PURIFICATION, CLEANSING AGENT, CARRIER, AGENT FOR EXTENDED RELEASE OF DRUGS, CELL CULTURE SCAFFOLD MATERIAL, MASK, CARBON/POLYMER COMPOSITE, ADSORPTIVE SHEET, AND FUNCTIONAL FOOD". Each of these applications is hereby incorporated by reference in its entirety.

TECHNICAL FIELD

The present invention relates to porous carbon materials, as well as to adsorbents, oral adsorbents, medical adsorbents, filler for blood purification columns, water purification adsorbents, cleansing agents, carriers, sustained release pharmaceuticals, cell culture scaffolds, masks, carbon/polymer composites, adsorbent sheets and functional foods using the porous carbon materials.

BACKGROUND ART

Activated carbons are porous carbon materials in which the fine pores of 2 nm or less called "micropores" exist dominantly. Up to now, various applications utilizing excellent adsorption properties of such activated carbons have been put to practical use. Furthermore, in improvement of performance of the applications and in development of new applications (adsorbents, oral adsorbents, medical adsorbents, filler for blood purification columns, water purification adsorbents, cleansing agents, carriers, sustained release pharmaceuticals, cell culture scaffolds, masks, carbon/polymer composites, adsorbent sheets and functional foods) as porous carbon materials, formation of "mesopores" and "macropores" leading to the micropores has been drawing attention (for example, see Japanese Unexamined Patent Application Publication Nos. 2004-182511 and 2004-345921).

Citation List

Patent Document 1: Japanese Unexamined Patent Application Publication No. 2004-182511
Patent Document 2: Japanese Unexamined Patent Application Publication No. 2004-345921

SUMMARY OF INVENTION

Problem to be Solved by the Invention

However, the activated carbons by the related art, in which, the micropores of 2 nm or less are dominant, were only capable of adsorbing organic molecules of small molecular weight mainly. That is, organic molecules and proteins of larger molecular weight would not be able to enter the fine pores, and would be difficult to be adsorbed by the activated carbons. In particular, as far as the inventors have investigated, a carbon material that is able to adsorb large proteins having molecular weight of 10,000 or more, or 50,000 or more, has not been known.

Therefore, an object of the present invention is to provide a porous carbon material that is surely able to adsorb organic molecules and proteins of larger molecular weight, and to provide an adsorbent, an oral adsorbent, a medical adsorbent, filler for blood purification columns, a water purification adsorbent, a cleansing agent, a carrier, a sustained release pharmaceutical, a cell culture scaffold, a mask, a carbon/polymer composite, an adsorbent sheet and a functional food using such a porous carbon material.

Means for Solving the Problem

A porous carbon material according to a first embodiment of the present invention for achieving the above object uses peat as a raw material, and has a total of volumes of fine pores having a diameter of from $1 \times 10^{-8}$ m to $2 \times 10^{-7}$ m, obtained by non-localized density functional theory method (NLDFT method), of 0.5 cm$^3$/g or more.

A porous carbon material according to a second embodiment of the present invention for achieving the above object uses peat as a raw material, and has at least one peak in the range of 3 nm to 20 nm, in a pore diameter distribution obtained by a non-localized density functional theory method, in which a ratio of a total of volumes of fine pores which have pore diameters in the range of 3 nm to 20 nm, with respect to a sum total of volumes of all fine pores, is 0.3 or more.

A porous carbon material according to a third embodiment of the present invention for achieving the above object uses peat as a raw material, and has a volume of fine pores obtained by BHJ method of 0.5 cm$^3$/g or more.

An adsorbent of the present invention for achieving the above object includes a porous carbon material according to the first to third embodiments of the present invention including various desirable modes described above. Here, the adsorbent of the present invention may be in a form to adsorb the molecules (or organic substances) having a number average molecular weight of from $1 \times 10^2$ to $1 \times 10^6$, desirably the molecules (or organic substances) having a number average molecular weight of from $1 \times 10^3$ to $1 \times 10^6$, more desirably the molecules (or organic substances) having a number average molecular weight of from $1 \times 10^4$ to $1 \times 10^6$, and still more desirably, the molecules (or organic substance) having a number average molecular weight of $1 \times 10^6$. Alternatively, an adsorbent that adsorbs α-amylase, an adsorbent that adsorbs lysozyme, or, an adsorbent for cigarette filters that adsorbs benzopyrene of the present invention for achieving the above object includes a porous carbon material according to the first to third embodiments of the present invention including various desirable modes described above.

An oral adsorbent, a medical adsorbent, filler for blood purification columns, a water purification adsorbent, a cleansing agent that adsorbs fatty acids, a carrier for carrying pharmaceuticals, a sustained release pharmaceutical and a cell culture scaffold of the present invention for achieving the above object include a porous carbon material according to the first to third embodiments of the present invention including various desirable modes described above.

A mask of the present invention for achieving the above object has an adsorbent which includes a porous carbon material according to the first to third embodiments of the present invention including various desirable modes described above.

A carbon/polymer composite of the present invention for achieving the above object includes a porous carbon material according to the first to third embodiments of the present invention including various desirable modes described above, and a binder.

An adsorbent sheet of the present invention for achieving the above object is made up with a sheet member which includes a porous carbon material according to the first to third embodiments of the present invention including various desirable modes described above, and with a support member to support the sheet member.

A functional food of the present invention for achieving the above object contains a porous carbon material according to the first to third embodiments of the present invention including various desirable modes described above.

Effect of the Invention

In the porous carbon materials according to the first to third embodiments of the present invention, or, the adsorbents, the oral adsorbents, the medical adsorbents, the filler for blood purification columns, the water purification adsorbents, the cleansing agents, the carriers, the sustained release pharmaceuticals, the cell culture scaffolds, the masks, the carbon/polymer composites, the adsorbent sheets and the functional foods of the present invention, which uses such porous carbon materials, peat is included as a raw material, and the volume of the fine pores having predetermined diameters is specified. Hence, desired substances, more specifically, in addition to organic molecules and proteins of small molecular weight; the organic molecules and proteins of larger molecular weight can surely be adsorbed with high efficiency.

Figure 3:
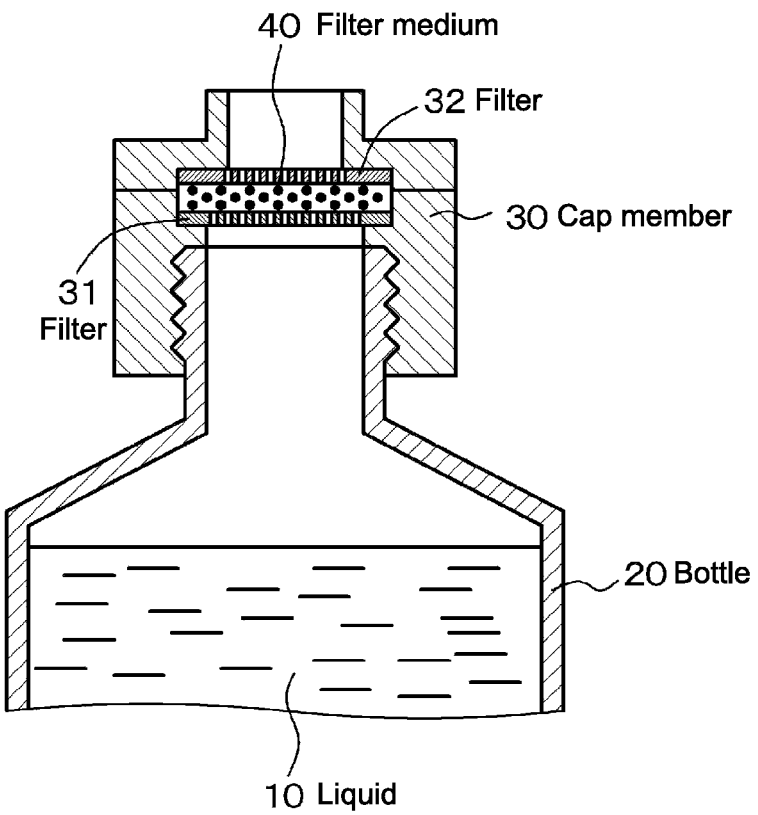
Figure 3:
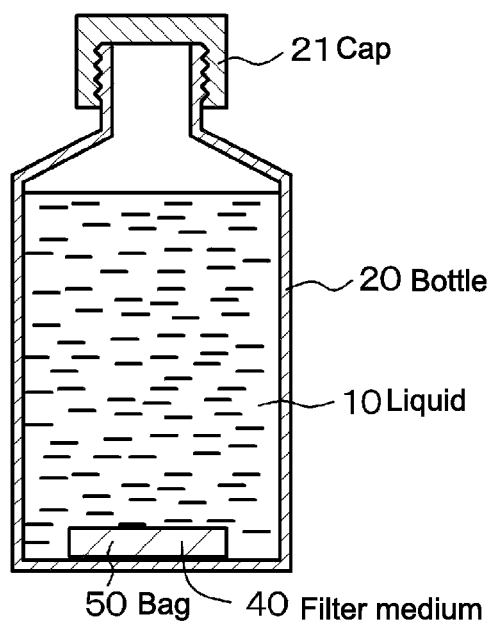

(A) and (B) of FIG. 3 are a schematic partial sectional view and a schematic sectional view of a bottle in Example 3.

Figure 4:
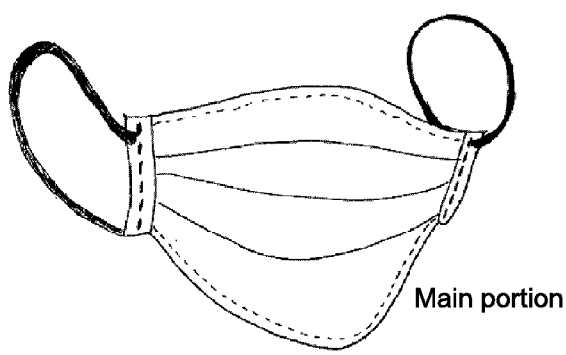
Figure 4:
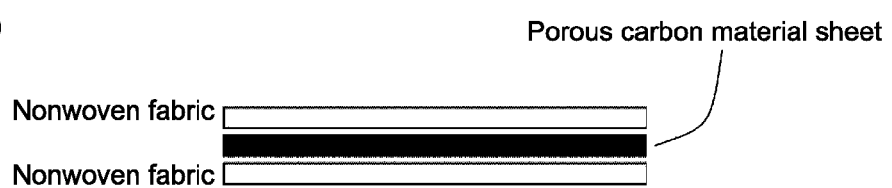

(A) and (B) of FIG. 4, respectively, are a schematic diagram of an anti-pollinosis mask of Example 6 and a diagram showing a schematic sectional structure of a main portion of the anti-pollinosis mask.

MODES FOR CARRYING OUT THE INVENTION

Hereinafter, with reference to drawings, the present invention will be described based on Examples. However, the present invention is not limited to the Examples. Various kinds of numerical values and materials in the Examples are illustrations. Description will be carried out in the following order.

1. Descriptions overall, of porous carbon materials according to first to third embodiments of the present invention, and of adsorbent, oral adsorbent, medical adsorbent, filler for blood purification columns, water purification adsorbent, cleansing agent, carrier, sustained release pharmaceutical, cell culture scaffold, mask, carbon/polymer composite, adsorbent sheet and functional food of the present invention 2. Example 1 (porous carbon materials according to first to third embodiments of the present invention, and adsorbent of the present invention)

3. Example 2 (oral adsorbent, medical adsorbent, filler for blood purification columns and cleansing agent of the present invention)

4. Example 3 (water purification adsorbent of the present invention)

5. Example 4 (carrier for carrying pharmaceuticals, and sustained release pharmaceutical, of the present invention)

6. Example 5 (cell culture scaffold of the present invention)

7. Example 6 (mask, carbon/polymer composite and adsorbent sheet of the present invention)

8. Example 7 (functional food of the present invention)

9. Example 8 (porous carbon material composite which is modification of Example 1), and others

[Descriptions Overall, of Porous Carbon Materials According to First to Third Embodiments of the Present Invention, and of Adsorbent, Oral Adsorbent, Medical Adsorbent, Filler for Blood Purification Columns, Water Purification Adsorbent, Cleansing Agent, Carrier, Sustained Release Pharmaceutical, Cell Culture Scaffold, Mask, Carbon/Polymer Composite, Adsorbent Sheet and Functional Food of the Present Invention]

In the porous carbon material according to the first to third embodiments of the present invention including various desirable modes described above, or, in the adsorbents, the oral adsorbents, the medical adsorbents, the filler for blood purification columns, the water purification adsorbents, the cleansing agents, the carriers, the sustained release pharmaceuticals, the cell culture scaffolds, the masks, the carbon/polymer composites, the adsorbent sheets and the functional foods of the present invention (hereinafter, in some cases, these are generically simply referred to as "the present invention"), peat (also called peat or turf) is used as the raw material of the porous carbon material; and specifically, the porous carbon material can be obtained by activating a substance (referred to as a "porous carbon material precursor") that has been obtained by subjecting the peat to a high-temperature heat treatment in an inert gas (nitrogen gas, argon gas or the like) or under vacuum. The peat may undergo a pretreatment such as washing (to allow various minerals to elute) after the above-mentioned high-temperature heat treatment. The peat may be pulverized to a desired particle size, and may be classified, as desired. In addition, the peat may be pre-washed. Alternatively, the obtained porous carbon material precursor or porous carbon material may be pulverized to a desired particle size, and may be classified, as desired. Or, the porous carbon material after the activation treatment may be pulverized to a desired particle size, and may be classified, as desired. Further, the finally obtained porous carbon material may be subjected to sterilization treatment. Hereinafter, the porous carbon materials according to first to third embodiments of the present invention may be generically referred to as a "porous carbon material in the present invention".

As a method of activation treatment, a gas activation method and a chemical activation method can be mentioned. Here, the gas activation method is a method by using oxygen, water vapor, carbon dioxide, air or the like as an activator, and by heating a porous carbon material under such an atmosphere, at 700° C. to 1400° C., desirably at 700° C. to 1000° C., and more desirably at 800° C. to 950° C., for several tens of minutes to several hours, so that a fine structure is developed due to volatile components or carbon molecules in the porous carbon material. More specifically, a heating temperature may be appropriately selected based on specifications of peat to use, a type and a concentration of gas, and the like. A chemical activation method is a method in which in place of oxygen or water vapor used in the gas activation method, zinc chloride, iron chloride, calcium phosphate, calcium hydroxide, magnesium carbonate, potassium carbonate, sulfuric acid or the like is used to activate, the resultant is washed with hydrochloric acid, pH of which is adjusted with an alkaline aqueous solution, and the resultant is dried.

On a surface of a porous carbon material in the present invention, a chemical treatment or a molecular modification may be applied. As a chemical treatment, for example, a treatment in which carboxyl groups are generated on the surface by a nitric acid treatment can be mentioned. Further, by conducting a treatment the same as the activation treatment with water vapor, oxygen, alkali, or the like on the surface of the porous carbon material, various kinds of functional groups such as a hydroxyl group, a carboxyl group, a ketone group and an ester group can be generated. Further, by reacting with a chemical species or a protein having a hydroxyl group, a carboxyl group, an amino group, or the like, which is capable of reacting with a porous carbon material, a molecular modification can be conducted.

The porous carbon materials in the present invention have many fine pores. In the fine pores, "micropores" having a pore diameter smaller than 2 nm, "mesopores" having a pore diameter from 2 nm to 50 nm, and "macropores" having a pore diameter exceeding 50 nm are included.

In the porous carbon materials in the present invention, it is desirable that a value of a specific surface area by a nitrogen BET method (hereinafter, in some cases, simply referred to as "value of specific surface area") is 10 $m^2/g$ or more, more desirably, 100 $m^2/g$ or more, and still more desirably, 400 $m^2/g$ or more.

Examples of the types of usage of the adsorbents of the present invention include the use in a form of a sheet, the use in a state of being filled in a column or a cartridge, the use in a state of being formed into a desired shape with a binder (a binding agent) or the like, and the use in a state of powder. In the case where the adsorbent is used as that dispersed in a solution, a surface of the adsorbent may be subjected to hydrophilic or hydrophobic treatment, to be used. Alternatively, as described above, the porous carbon material in the present invention can be used as filler (an absorbing agent) for blood purification columns, as water purification adsorbent that purifies water, and can also be used as a cleansing agent. The filler for blood purification columns, the water purification adsorbent and the cleansing agent of the present invention can have a constitution and structure of the well-known. The types of usage may be the same as the above, or, may be appropriately selected and determined depending on the forms of the filler for blood purification columns, the water purification adsorbent or the cleansing agent.

Specific examples of the types of usage of the water purification adsorbents of the present invention include the use in a form of a sheet, the use in a state of being filled in a column or a cartridge, the use in a state of being housed in a water-permeating bag, the use in a state of being formed into a desired shape with a binder (a binding agent) or the like, and the use in a state of powder. In the case where the water purification adsorbent is used as that dispersed in water (a solution), a surface of the water purification adsorbent can be subjected to hydrophilic or hydrophobic treatment, to be used.

An apparatus suitable for incorporating the water purification adsorbent (filter medium) of the present invention such as a purification apparatus, specifically, a water cleaner (hereinafter, in some cases, referred to as "water cleaner in the present invention") may have a structure (combined use of the water purification adsorbent of the present invention and a filtration membrane) that further includes a filtration membrane (for example, hollow fiber membrane or flat membrane having 0.4 μm to 0.01 μm holes), a structure (combined use of the water purification adsorbent of the present invention and a reverse osmosis membrane) that further includes a reverse osmosis membrane (RO), a structure (combined use of the water purification adsorbent of the present invention and a ceramic filter medium) that further includes a ceramic filter medium (ceramic filter medium having fine pores), or a structure (combined use of the water purification adsorbent of the present invention and an ion exchange resin) that further includes an ion exchange resin.

As types of the water cleaners of the present invention, a continuous water cleaner, a batch water cleaner and a reverse osmosis membrane water cleaner can be mentioned, or a faucet-coupled water cleaner in which a water cleaner body is directly attached to a tip part of a water faucet, a stationary water cleaner (also referred to as top sink water cleaner or table top water cleaner), a water faucet-integrated water cleaner in which a water cleaner is incorporated in a water faucet, a under-sink water cleaner that is installed in a sink of a kitchen (built-in water cleaner), a pot water cleaner in which a water cleaner is incorporated in a container such as a pot and a pitcher (pitcher water cleaner), a central water cleaner that is directly attached to a water pipe after a water meter, a portable water cleaner and a straw water cleaner can be mentioned. The water cleaner in the present invention can have a constitution and structure the same as those of a water cleaner of the past. In the water cleaner in the present invention, the water purification adsorbent (porous carbon material) of the present invention can be used in a cartridge, for example, and to the cartridge, a water inlet and a water outlet may be provided. The "water" that is a target of purification in the water cleaner in the present invention is not limited to the "water" defined in "3. Terms and Definitions" of JIS 53201: 2010 "Testing methods for household water cleaners".

Alternatively, as a member suitable for incorporating suitable for incorporating the water purification adsorbent (filter medium) of the present invention, a cap or a cover in a bottle (so-called PET bottle), a laminate container, a plastic container, a glass container, a glass bottle, and the like, which are provided with a cap or a cover can be mentioned. Here, when a water purification adsorbent of the present invention is disposed inside a cap or a cover, and a liquid or water (drinkable water, a lotion, or the like) in a bottle, a laminate container, a plastic container, a glass container, a glass bottle or the like is passed through the water purification adsorbent of the present invention disposed inside the cap or cover and is drunk, or used, the filtrate water can be purified. Alternatively, a form in which the water purification adsorbent of the present invention is housed in a bag having water permeability, and the bag is put in a liquid or water (drinkable water, a lotion, or the like) inside various kinds of containers such as a bottle (so-called PET bottle), a laminate container, a plastic container, a glass container, a glass bottle, a pot and a pitcher, can be adopted.

Dosage forms of the oral adsorbents and the medical adsorbents of the present invention may take any forms, of powders, granules, tablets, sugar-coated tablets, capsules, suspensions, emulsions and the like. In the case where it is taken as a capsule preparation, a capsule made from an enteric material in addition to usual gelatins may be used. In the case where it is a tablet, an excipient such as lactose and starch; a binder such as hydroxypropyl cellulose, Arabic gum and starch paste; wax such as magnesium stearate; a lubricant such as talc; disintegrators such as celluloses; and the like. In addition, in other ways, it may be used as multiple agents with alumina or silica components. The porous carbon material in the present invention can be used for selectively adsorbing various unwanted molecules from the body. That is, as described above, the porous carbon material in the present invention can be used as oral adsorbents or medical adsorbents such as pharmaceuticals for internal use, which is useful for therapy and prophylaxis of diseases. Here, in addition to using the adsorbent of the present invention as an adsorbent that adsorbs α-amylase, an adsorbent that adsorbs lysozyme or an adsorbent for cigarette filters that adsorbs benzopyrene, it can be used as an adsorbent to adsorb indole; uric acid; adenosine; 3-methylindole; tryptophan; indican; theophylline; inosine 5-1 phosphoric acid disodium salt; fatty acids (specifically, for example, oleic acid, stearic acid, myristic acid, squalene and cholesterol); dyes; hydrophobic molecules; molecules having a number average molecular weight of from $1 \times 10^3$ to $1 \times 10^6$, organic substances (for example, organic molecules, or, proteins); ammonia; urea; dimethylamine; guanidine compounds such as methyl guanidine; sulfur-containing amino acids; phenol; p-cresol; oxalic acid; homocysteine; guanidino succinic acid; myo-inositol; indoxyl sulfuric acid; pseudouridine; cyclic adenosine monophosphoric acid; creatinine; β-aminoisobutyric acid; octopamine; α-amino butyric acid; parathyroid hormones; β2-microglobulin; ribonuclease; natriuretic hormones; or water-soluble basic and amphoteric substances such as aspartic acid and arginine. Besides, the adsorbent of the present invention can be used as an adsorbent to adsorb purine and derivatives of purine; adenine and guanine which are purine bases; guanosine and inosine which are purine nucleosides; or adenylic acid, guanylic acid and inosinic acid which are purine nucleotides. Furthermore, the adsorbent of the present invention can be used as an adsorbent to adsorb oligonucleotides and polynucleotides which are low molecular or polymer nucleic acids, and is also able to adsorb polyamines, 3-deoxyglucosone or various peptide hormones. In particular, the adsorbent of the present invention is excellent in adsorption of proteins of large molecular weight as the following. That is, the adsorbent of the present invention can be used as an adsorbent to adsorb granulocyte inhibitory proteins (GIP), degranulation inhibitory proteins (DIP) and chemotaxis inhibitory proteins; and furthermore, examples of the proteins of large molecular weight can include various enzymes; proteins that form the living structure such as collagen and keratin; protein hormones, and receptors thereof; proteins that are involved in intracellular signaling; proteins that make up muscles such as actin and myosin; antigen/antibody proteins; proteins that are contained as nutrients in eggs, seeds, milk or the like; proteins in blood such as albumin; proteins that are involved in fluorescence such as GFP and RFP; and the like. Besides, the adsorbent of the present invention can be used as an adsorbent to adsorb carbamylated hemoglobin; glycation end products; granulocyte/monocyte function-inhibiting substances; oxidation-promoting substances; or the like. Or, the adsorbent of the present invention can be used as an adsorbent to adsorb 1,1-diphenyl-2-picrylhydrazyl (DPPH, number average molecular weight: 394); tyrosine (tylosin, number average molecular weight: 394); or microcystins. Incidentally, the adsorbent that adsorbs α-amylase can be applied to a model for a study of adsorption properties to adsorb a protein such as an inflammatory cytokine which causes Crohn's disease or the like (a pseudo inflammatory cytokine).

In addition, the porous carbon material in the present invention may adsorb fatty acids, dyes, or hydrophobic molecules, for example. Specific examples of the fatty acids include oleic acid, stearic acid, myristic acid, squalene, (oil belonging to terpenoids), cholesterol (biosynthesized from squalene) and stearic acid monoglycerin. Specific examples of the dyes include general legal pigments (tar color) including Lithol Rubine BCA (Red No. 202); that is, Amaranth (Red No. 2), New Coccine (Red No. 102), Lithol Rubine B (Red No. 201), Lithol Red CA (Red No. 206), Rhodamine B (Red No. 231), Deep Maroon (Red No. 220), Fast Acid Magenta (Red No. 227), Violamine R (Red No. 401), Scarlet Red NF (Red No. 501), Fast Red S (Red No. 506), Dibromofluorescein (Orange No. 201), Diiodofluorescein (Orange No. 206), Hanza Orange (Orange No. 401), Tartrazine (Yellow No. 4), Fluorescein (Yellow No. 201), Benzidine Yellow G (Yellow No. 205), Hanza Yellow (Yellow No. 401), Metanil Yellow (Yellow No. 406), Fast Green FCF (Green No. 3), Alizarine Cyanine Green F (Green No. 201), Naphthol Green B (Green No. 401), Brilliant Blue FCF (Blue No. 1), Indigo (Blue No. 201), Sudan Blue B (Blue No. 403), Resorcin Brown (Brown No. 201), Alizurine Purple SS (Purple No. 201) and Naphthol Blue Black (Black No. 401). The "hydrophobic molecules" can be defined to mean sebum which is present on the human skin surface, as well as oils and dirt which may adhere to skin or clothing in daily lives, which specifically means sebum and fats and oils which include glycerol fatty acid esters as a component; lipids such as simple lipids, complex lipids and derived lipids; organic acids which are components of wax or the like; especially, oil components in general which may be present on the human skin surface (fatty acids in a broad sense); and also means fatty acids in a narrow sense which include a linear or branched chain or a cyclic structure such as saturated fatty acids and unsaturated fatty acids. The adsorbent that adsorbs fatty acids, the adsorbent that adsorbs dyes and the cleansing agent of the present invention (cleaning agent, adsorbent for cosmetic or washing) are those which remove stain components such as sweat, oil and fat, and lipsticks, which may further have a skin-conditioning effect.

Besides, as described above, the carrier of the present invention for carrying pharmaceuticals can be made up with the porous carbon material in the present invention, and in such a case, the carrier can have a constitution and structure of the well-known. With 100 parts by weight of the porous carbon material in the present invention; by allowing the porous carbon material in the present invention to adsorb to carry 1 to 200 parts by weight of a pharmaceutical, a composite which is capable of releasing the pharmaceutical (a pharmaceutical/carrier composite capable of appropriately controlling the drug release rate, as a sustained release pharmaceutical) can be obtained. Here, such a pharmaceutical/carrier composite (sustained release pharmaceutical) may be an embodiment which is made up of the porous carbon material in the present invention and a pharmaceutical, in which, a weight ratio of the porous carbon material and the pharmaceutical is 1 to 200 parts by weight of the pharmaceutical to 100 parts by weight of the porous carbon material in the present invention. The sustained release pharmaceutical can have a constitution and structure of the well-known.

Examples of the pharmaceuticals to be adsorbed to be carried by the porous carbon material in the present invention include organic molecules, polymer molecules and proteins. Specific examples thereof include pentoxifylline, prazosin, acyclovir, nifedipine, diltiazem, naproxen, ibuprofen, flurbiprofen, ketoprofen, fenoprofen, indomethacin, diclofenac, fentiazac, estradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-ASA, quinidine, perindopril, morphine, pentazocine, paracetamol, omeprazole, metoclopramide, aspirin and metformin. From the viewpoint of systemic and local therapies, various hormones (for example, insulin, estradiol, etc.), therapeutic agents for asthma (for example, albuterol, etc.), therapeutic agents for tuberculosis (for example, rifampicin, ethambutol, streptomycin, isoniazid, pyrazinamide, etc.), therapeutic agents for cancer (for example, cisplatin, carboplatin, adriamycin, 5-FU, paclitaxel, etc.) and therapeutic agents for hypertension (for example, clonidine, prazosin, propranolol, labetalol, bunitrolol, reserpine, nifedipine, furosemide, etc.) can be mentioned. As the carrier is suitable in particular for carrying protein pharmaceuticals of large molecular weight, examples of the pharmaceuticals may include, but are not limited to, antibody pharmaceuticals such as infliximab, adalimumab, tocilizumab, certolizumab pegol, natalizumab, rituximab, gemtuzumab, alemtuzumab, ibritumomab, tiuxetan, tositumomab, trastuzumab, bevacizumab, cetuximab, panitumumab, cetuximab, abciximab, palivizumab, ranibizumab and omalizumab. Further, by dissolving the pharmaceutical in an organic solvent which is capable of dissolving such pharmaceuticals, allowing the porous carbon material in the present invention to be immersed into the resultant solution, followed by removing the solvent and excess solute, a porous carbon material/pharmaceutical composite can be obtained. Specific examples of the solvents include water, methyl alcohol, ethyl alcohol, isopropyl alcohol, butyl alcohol, acetone, ethyl acetate, chloroform, 2-chloromethane, 1-chloromethane, hexane, tetrahydrofuran, pyridine and the like.

The porous carbon material in the present invention can be used as a cell culture scaffold (cell culture material). Besides, for example, to adsorbents for various masks such as antipollinosis masks, the porous carbon material in the present invention can be applied, and for example, proteins can be adsorbed thereto. The adsorbent sheet of the present invention, for example, has a structure in which a sheet member or the carbon/polymer composite of the present invention is sandwiched between a support member (for example, nonwoven fabric) made of cellulose and another support member (for example, nonwoven fabric). In addition, in the carbon/polymer composite of the present invention, a binder thereof is made up of a polymer. Here, examples of the binders include carboxy nitrocellulose. From the adsorbent sheet or the carbon/polymer composite of the present invention, for example, a filter for an air purifier, a mask, a protective glove and protective shoes can be formed.

In the functional food of the present invention, other ingredients, for example, an excipient, a binder, a disintegrating agent, a lubricant, a diluent, a flavoring substance, a preserving agent, a stabilizer, a colorant, a perfume, vitamins, a color former, a gloss agent, a sweetener, a bittering agent, an acidulant, an umami seasoning, a fermented seasoning, an antioxidant, a yeast, a yeast extract, and an enrichment may be contained. Examples of forms of the functional foods include a powdery shape, a solid-like shape, a tablet-like shape, a particulate shape, a granular shape, a capsular shape, a creamy shape, a sol-like shape, a gel-like shape and a colloidal shape. In addition, the porous carbon material of the present invention can be contained in other products such as health foods, nutritional supplements, health supplements, Foods with Nutrient Function Claims, Foods for Specified Health Use, quasi-drugs and pharmaceuticals as well. The health foods, the nutritional supplements and the health supplements are defined by the Food Sanitation Law; the Foods with Nutrient Function Claims and the Foods for Specified Health Use are defined by the Health Promotion Law and the Food Sanitation Law; the quasi-drugs and the pharmaceuticals are defined by the Pharmaceutical Affairs Law.

Besides, the porous carbon material in the present invention can be used in porous carbon material composites such as transdermal drugs; cosmetic ingredients or ingredients having moisturizing effect and/or anti-oxidation effect; and fresheners. Examples of the cosmetic ingredients include a substance that contains a hydrophobic beauty component (for example, daidzein, genistein, collagen, sericin or fibroin); and the ingredients having moisturizing effect and/or anti-oxidation effect include effective ingredients contained in lotions such as hyaluronic acid, astaxanthin, tocopherol, trolox and coenzyme Q10. Examples of the fresheners include released substances such as limonene, menthol, linalool and vanillin. For example, the porous carbon material composite can be obtained by a method employing a liquid substance as these released substances, in which the porous carbon material is immersed into the liquid substance and is dried. However, it is not limited to such a method.

The nitrogen BET method is a method in which nitrogen as adsorbate molecules is adsorbed onto and desorbed from the adsorbent (here, the porous carbon material) to measure an adsorption isotherm, and the measurement data is analyzed based on a BET formula represented by the formula (1). Based on this method, a specific surface area, a fine pore volume and the like can be calculated. Specifically, in the case of calculating the specific surface area by a nitrogen BET method, first, nitrogen as adsorbate molecules is adsorbed onto and desorbed from the adsorbent (porous carbon material) to obtain the adsorption isotherm. Then, from the adsorption isotherm thus obtained, $[p/\{V_a(p_0-p)\}]$ is calculated based on the formula (1) or on the formula (1') obtained by modification of the formula (1), and the calculation result is plotted against the equilibrium relative pressure ($p/p_0$). Next, regarding the plot as a straight line, the inclination s ($=[(C-1)/(C \cdot V_m)]$) and the intercept i ($=[1/(C \cdot V_m)]$) of the straight line are calculated based on the least squares method. Then, from the inclination s and the intercept i thus obtained, $V_m$ and C are calculated based on the formula (2-1) and the formula (2-2). Further, the specific surface area $a_{sBET}$ is calculated from $V_m$ based on the formula (3) (see the manual for BELSORP-mini and BELSORP analysis software, made by BEL Japan, Inc., pp. 62 to 66). Incidentally, the nitrogen BET method is a measuring method according to the "Measuring method for specific surface area of fine ceramic powders by gas adsorption BET method" defined by JIS R 1626-1996.

$$V_a = (V_m C \cdot p)/[(p_0-p)\{1+(C-1)(p/p_0)\}] \tag{1}$$

$$[p/\{V_a(p_0-p)\}] = [(C-1)/(C \cdot V_m)](p/p_0) + [1/(C \cdot V_m)] \tag{1'}$$

$$V_m = 1/(s+i) \tag{2-1}$$

$$C = (s/i)+1 \tag{2-2}$$

$$a_{sBET} = (V_m \cdot L \cdot \sigma)/22414 \tag{3}$$

where
$V_a$: adsorption amount;
$V_m$: adsorption amount of monomolecular layer;
p: pressure of nitrogen at equilibrium;
$p_0$: saturated vapor pressure of nitrogen;
L: Avogadro's number; and
σ: adsorption cross section of nitrogen.

In the case of calculating the fine pore volume $V_p$ by the nitrogen BET method, for example, linear interpolation is applied to the adsorption data of the adsorption isotherm obtained, and the adsorption amount V at a relative pressure set by a fine pore volume calculation relative pressure is obtained. From this adsorption volume V, the fine pore volume $V_p$ can be calculated based on the formula (4) (see the Manual for BELSORP-mini and BELSORP analysis software, made by BEL Japan, Inc., pp. 62 to 65). Incidentally, the fine pore volume based on the nitrogen BET method may hereinafter be referred to simply as "fine pore volume").

$$V_p = (V/22414) \times (M_g/\rho_g) \quad (4)$$

where
V: adsorption amount at relative pressure;
$M_g$: molecular weight of nitrogen; and
$\rho_g$: density of nitrogen.

The pore diameter of mesopores can, for example, be calculated as a pore size distribution from the fine pore volume variation rate relative to the pore diameter, based on the BJH method. The BJH method is a method that is widely used as a pore size distribution analyzing method. In the case of analyzing the pore size distribution based on the BJH method, first, nitrogen as adsorbate molecules is adsorbed onto and desorbed from an adsorbent (porous carbon material) to obtain a desorption isotherm. Next, based on the desorption isotherm thus obtained, a thickness of an adsorbed layer at the time of stepwise adsorption/desorption of adsorbate molecules from the condition where the fine pores are filled with the adsorbate molecules (for example, nitrogen) and an inside diameter (twice the core radius) of the pores generated in that instance are obtained, then the fine pore radius $r_p$ is calculated based on the formula (5), and the fine pore volume is calculated based on the formula (6). Then, based on the fine pore radius and the fine pore volume, the fine pore volume variation rate $(dV_p/dr_p)$ relative to the pore diameter $(2r_p)$ is plotted, whereby the pore size distribution curve is obtained (see the Manual for BELSORP-mini and BELSORP analysis software, made by BEL Japan, Inc., pp. 85 to 88).

$$r_p = t + r_k \quad (5)$$

$$V_{pn} = R_n dV_n - R_n \cdot dt_n \cdot c \cdot \Sigma A_{pj} \quad (6)$$

where $$R_n = r_{pn}^2 / (r_{kn} - 1 + dt_n)^2 \quad (7)$$

where
$r_p$: fine pore radius;
$r_k$: core radius (inside diameter/2) in the case where an adsorbed layer with a thickness t is adsorbed on the inner wall of fine pores with a fine pore radius $r_p$ at that pressure;
$V_{pn}$: fine pore volume when n-th adsorption/desorption of nitrogen is generated;
$dV_n$: variation in that instance;
$dt_n$: variation of thickness $t_n$ of the adsorbed layer when the n-th adsorption/desorption of nitrogen is generated;
$r_{kn}$: core radius in that instance;
c: constant; and
$r_{pn}$: pore diameter when the n-th adsorption/desorption of nitrogen is generated. Besides, $\Sigma A_{pj}$ is the integrated value of the area of wall surfaces of fine pores from j=1 to j=n−1.

The pore diameter of micropores can be calculated as a pore size distribution from the fine pore volume variation rate relative to the pore diameter, based on, for example, the MP method. In the case of analyzing the pore size distribution by the MP method, first, nitrogen is adsorbed onto the adsorbent (porous carbon material) to obtain an adsorption isotherm. Next, the adsorption isotherm is converted into fine pore volume relative to a thickness t of the adsorbed layer (plotted against t). Then, based on the curvature of the plot (variation of fine pore volume relative to variation in thickness t of adsorbed layer), a pore size distribution curve can be obtained (see the Manual for BELSORP-mini and BELSORP analysis software, made by BEL Japan, Inc., pp. 72 to 73 and p. 82).

In the non-localized density functional theory method (NLDFT method) specified in JIS Z8831-2: 2010 "A fine pore distribution and fine pore characteristics of powder (solid)—the second part: A method of measuring a mesopore and a macropore based on gas adsorption" and JIS Z8831-3: 2010 "A pore diameter distribution and fine pore characteristics of powder (solid)—the third part: A method of measuring a micropore based on gas adsorption", a software that comes with an automatic specific surface area/fine pore distribution measuring apparatus "BELSORP-MAX" manufactured by BEL JAPAN, INC. is used as analysis software. A model is formed so as to have a cylindrical shape and carbon black (CB) is assumed as the prerequisite, and a distribution function of a fine pore distribution parameter is set as "no-assumption". The smoothing is carried out ten times for the resulting distribution data.

Example 1

Example 1 relates to a porous carbon material according to the first to third embodiments of the present invention, an adsorbent of the present invention, an adsorbent of the present invention that adsorbs α-amylase, an adsorbent of the present invention that adsorbs lysozyme, and an adsorbent for cigarette filters that adsorbs benzopyrene, of the present invention.

A porous carbon material of Example 1 uses peat as a raw material. As described in accordance with configurations of the porous carbon material according to the first embodiment of the present invention, in the porous carbon material of Example 1, a total of volumes $V_{10-200}$ 200 of fine pores having a diameter of from $1 \times 10^{-8}$ m to $2 \times 10^{-7}$ m, obtained by non-localized density functional theory method (NLDFT method), is 0.5 cm$^3$/g or more. Further, as described in accordance with configurations of the porous carbon material according to the second embodiment of the present invention, the porous carbon material of Example 1 has at least one peak in the range of 3 nm to 20 nm, in a pore diameter distribution obtained by a non-localized density functional theory method, in which a ratio $(V_{3-20}/V_{Total})$ of a total of volumes $V_{3-20}$ of fine pores which have pore diameters in the range of 3 nm to 20 nm, with respect to a sum total of volumes of all fine pores $V_{Total}$, is 0.3 or more.

Alternatively, as described in accordance with configurations of the porous carbon material according to the third embodiment of the present invention, in the porous carbon material of Example 1, a volume $V_{BJH}$ of fine pores obtained by BHJ method is 0.5 cm$^3$/g or more.

Figure 1:
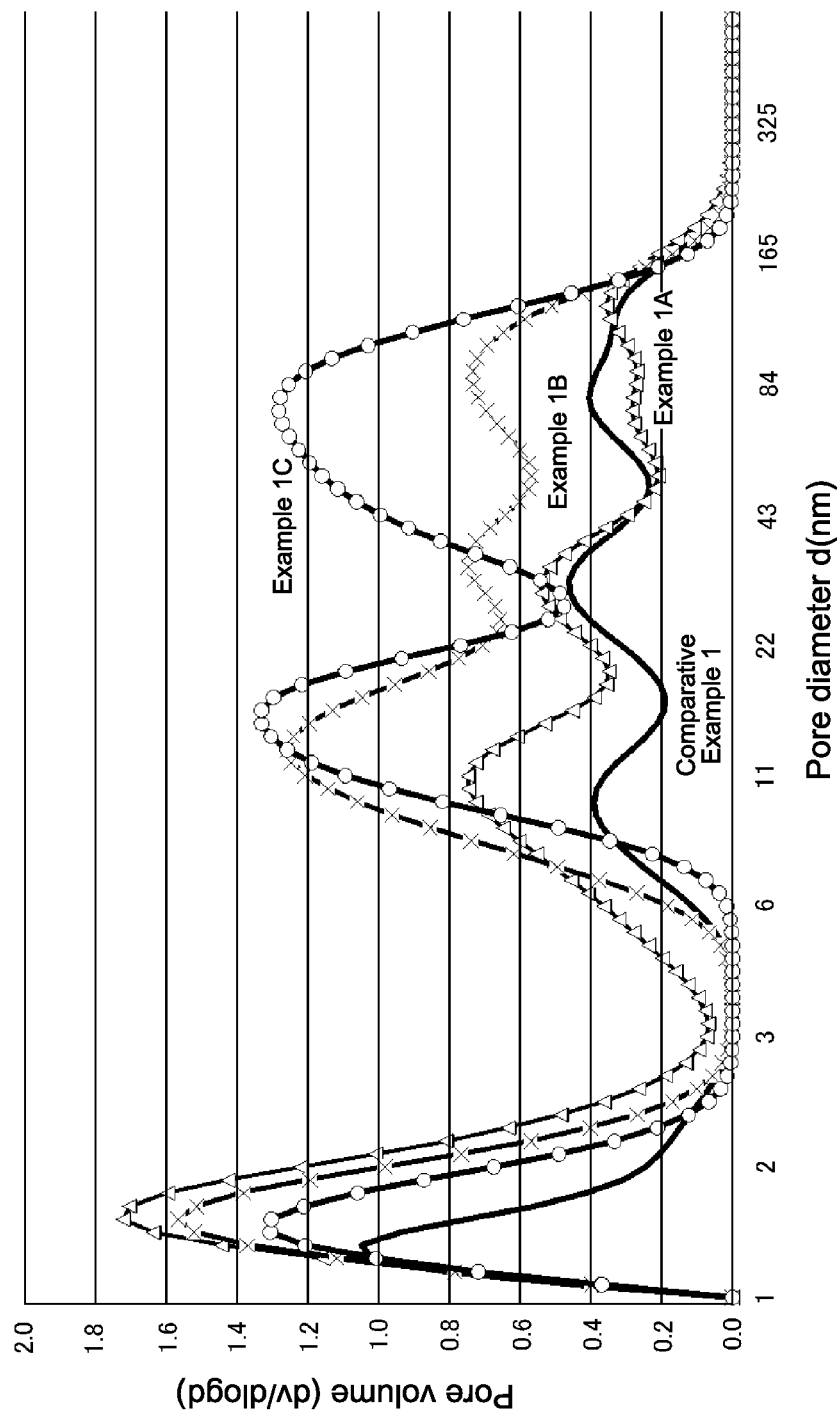
FIG. 1 is a graph showing measurement results of pore diameter distribution obtained based on a non-localized density functional method, of porous carbon materials of Examples 1A, 1B and 1C and a porous carbon material precursor of Comparative Example 1.

In Example 1, the porous carbon material was obtained by activating a substance (which is a porous carbon material precursor, and will be referred to as "Comparative Example 1") that had been obtained by subjecting the peat to a high-temperature heat treatment in an inert gas (nitrogen gas, argon gas or the like) or under vacuum; and by further subjecting the resultant material to a pretreatment such as washing (to allow various minerals to elute) after such a heat treatment. The activation treatment was by a gas activation method. Specifically, an activation treatment was carried out by using a tubular-type nitrogen atmosphere furnace and using water vapor as an activator under water vapor atmosphere, at 900° C. for 1 hour (Example 1A), 3 hours (Example 1B) or 5 hours (Example 1C). The results of measurement of fine pores and the like on the obtained porous carbon materials of Examples 1A, 1B and 1C and the porous carbon material precursor of Comparative Example 1 (hereinafter, these will be referred to as "specimens") are shown in Table 1 and in FIG. 1. FIG. 1 shows the measurement results of pore diameter distribution obtained based on a non-localized density functional method, in which, data represented by white triangles indicate Example 1A; data represented by "x" marks indicate Example 1B; data represented by white circles indicate Example 1C; and data represented by a solid curve indicate Comparative Example 1.

BELSORP-mini (manufactured by BEL JAPAN INC.) was used as a measurement instrument for obtaining the specific surface area and the fine pore volume, and a test for adsorbing and desorbing nitrogen was carried out. With regard to the measurement condition, a measurement equilibrium relative pressure ($p/p_0$) was set in the range of 0.01 to 0.99. Also, the specific surface area and the fine pore volume were calculated based on the BELSORP analysis software. In addition, the test for adsorbing and desorbing nitrogen was carried out by using the measurement instrument described above, thereby calculating the pore diameter distribution of the mesopores and the micropores based on both the BJH method and the MP method using the BELSORP analysis software. In addition, the automatic specific surface area/pore distribution measuring apparatus "BELSORP-MAX" manufactured by BEL JAPAN, INC. was used for the analysis based on the non-localized density functional theory method. It is noted that for the measurement, drying was carried out at 200° C. for 3 hours as a pretreatment for a specimen.

TABLE 1

| | unit | Ex. 1A | Ex. 1B | Ex. 1C | Comp. Ex. 1 |
|---|---|---|---|---|---|
| Sum total of volumes of all fine pores $V_{Total}$ | cm³/g | 1.078 | 1.433 | 1.520 | 0.886 |
| Volume of fine pores of 10 nm to 200 nm obtained by NLDFT method $V_{10-200}$ | cm³/g | 0.486 | 0.908 | 1.15 | 0.395 |
| Volume of fine pores of 3 nm to 10 nm obtained by NLDFT method $V_{3-20}$ | cm³/g | 0.32 | 0.47 | 0.42 | 0.19 |
| $V_{3-20}/V_{Total}$ | | 0.30 | 0.33 | 0.28 | 0.22 |
| Volume of fine pores obtained by BJH method $V_{BJH}$ | cm³/g | 0.60 | 0.99 | 1.15 | 0.43 |
| Specific surface area | m²/g | 872 | 903 | 836 | 688 |

Adsorption amounts of α-amylase (number average molecular weight: $5.5 \times 10^4$) and of lysozyme (number average molecular weight: $1.4 \times 10^4$) adsorbed by the porous carbon materials were measured. Specifically, phosphate buffer solutions of α-amylase or lysozyme having a concentration of 500 milligram/liter were prepared. Then, to each 10.0 milliliters of the prepared phosphate buffer solutions, 0.010 grams of each specimen of Examples 1A, 1B and 1C and Comparative Example 1 was added, followed by shaking for 3 hours at room temperature. After shaking, the specimen was removed from the phosphate buffer solution with the use of a membrane filter made of polytetrafluoroethylene with 500-µm pores. Then, an absorbance of the resultant filtrate was measured by UV-visible absorbance measurement to thereby obtain its molar concentration (referred to as "molar concentration after adsorption"). In addition, by comparing it with the molar concentration in the phosphate buffer solution before the addition of the specimen (referred to as "initial molar concentration"), the adsorption amount was calculated. The adsorption amount per gram of the specimen (milligram/gram) was calculated based on the following equation. The results are shown in Table 2.

In addition, adsorption amounts of Methylene blue (number average molecular weight: 320) and of Black 5 (number average molecular weight: 900) adsorbed by the porous carbon materials were measured. Aqueous solution concentrations of Methylene blue and Black 5 before adsorption were decided arbitrarily. Then, to each 50.0 milliliters of the prepared aqueous solutions, 0.010 grams of each specimen was added, followed by shaking for 3 hours at room temperature. After shaking, the specimen was removed from the aqueous solution with the use of the membrane filter made of polytetrafluoroethylene with 500-µm pores. Then, an absorbance of the resultant filtrate was measured by UV-visible absorbance measurement to thereby obtain its molar concentration after adsorption. In addition, by comparing it with an initial molar concentration before the addition of the specimen, the adsorption amount was calculated. The adsorption amount per gram of the specimen (milligram/gram) was calculated based on the following equation. The results are shown in Table 2.

(Adsorption amount per gram of specimen)=(Molecular weight of solute)×{(initial molar concentration)−(molar concentration after adsorption)}/ (amount of specimen per 1000 milliliters)

TABLE 2

| | α-amylase | Lysozyme | Black 5 | Unit: mg/g Methylene blue |
|---|---|---|---|---|
| Number average molecular weight | $5.5 \times 10^4$ | $1.4 \times 10^4$ | 900 | 373 |
| Ex. 1A | 143 | 160 | 262 | 348 |
| Ex. 1B | 254 | 277 | 408 | 390 |
| Ex. 1C | 312 | 317 | 441 | 379 |
| Comp. Ex. 1 | 99 | 91 | 128 | 240 |

From Table 2, the adsorption amounts of α-amylase and of lysozyme adsorbed by the porous carbon materials of Examples 1A, 1B and 1C were greater than the adsorption amounts of α-amylase and of lysozyme adsorbed by the porous carbon material precursor of Comparative Example 1; and furthermore, a longer steam activation time, that is, a larger volume $V_{10-200}$ of fine pores having a diameter of from $1 \times 10^{-8}$ m to $2 \times 10^{-7}$ m, and a larger value of $V_{Total}$, resulted in greater adsorption amounts. This indicates that a larger volume $V_{10-200}$ of fine pores having a diameter of from $1 \times 10^{-8}$ m to $2 \times 10^{-7}$ m and a larger value of $V_{Total}$ allow molecules or organic substances having large number average molecular weight to be absorbed better. That is, this indicates that the material adsorbs the molecules (or organic substances) having a number average molecular weight of from $1 \times 10^3$ to $1\times10^6$, and further indicates that it adsorbs the molecules (or organic substances) having a number average molecular weight of from $1\times10^4$ to $1\times10^6$ better, and further indicates that it adsorbs the molecules (or organic substances) having a number average molecular weight of $1\times10^6$ even better.

As described in the above, it was revealed that adsorption properties of porous carbon materials to adsorb molecules differ depending on differences in parameters such as volumes of fine pores of the porous carbon materials and pore diameter distributions. Further, in particular, there was a difference observed between the behavior of the porous carbon material on the adsorption of molecules of small molecular weight and the behavior of the porous carbon material on the adsorption of molecules of large molecular weight; and it was revealed that the porous carbon materials in Example 1 are able to adsorb substances having a high molecular weight better, as compared with the porous carbon material precursor (activated carbon) of Comparative Example 1. Therefore, by determining the relationship between a molecular weight of a molecule to be adsorbed and a parameter of the porous carbon material, the relationship with a production method or the like, based on various tests, it enables the porous carbon material to selectively adsorb the molecule. This can be expected to have great effects in various medical uses which require adsorption, for example.

Next, adsorption amounts of benzopyrene (number average molecular weight: 252) adsorbed by the porous carbon materials were measured. Specifically, a solution having a concentration of $4.58\times10^{-5}$ mole/liter was prepared using benzopyrene, distilled water and ethyl alcohol. Then, to 40.0 milliliters of the prepared solution, 0.010 grams of the porous carbon material (Example 1A, 1B or 1C) was added, followed by stirring for 1 hour at room temperature. After stirring, the porous carbon material was removed from the solution with the use of a membrane filter made of polytetrafluoroethylene. Then, an absorbance of the resultant filtrate was measured by UV-visible absorbance measurement, and a benzopyrene adsorption rate was calculated from the following equation, based on an absorbance of the prepared solution before the adsorption. Further, benzopyrene adsorption rates were determined in the same manner, on a commercially available peat coal as Comparative Example 1A and Kuraray Coal, which is an activated carbon manufactured by Kuraray Chemical Co., Ltd., as Comparative Example 1B. The results are shown in Table 3. When the adsorbents of Examples 1A to 1C were used as the adsorbents for cigarette filters to adsorb benzopyrene, the benzopyrene, which is highly-carcinogenic, was adsorbed thereto by high adsorption rate as compared with Comparative Examples 1A and 1B. That is, the adsorbents of Examples 1A to 1C were found to be capable of effectively adsorbing the molecules (or organic substances) having a number average molecular weight of the level of $1\times10^2$. Incidentally, the adsorbent to include benzopyrene may be mixed into the material forming the cigarette filter, or may be arranged as a layered adsorbent within the cigarette filter.

Benzopyrene adsorption rate (%)=100–(absorbance after adsorption/absorbance before adsorption× 100)

TABLE 3

| | Benzopyrene adsorption rate (%) |
| --- | --- |
| Example 1A | 94 |
| Example 1B | 96 |
| Example 1C | 94 |
| Comparative Example 1A | 79 |
| Comparative Example 1B | 52 |

Example 2

Example 2 relates to an oral adsorbent and a medical adsorbent of the present invention. In Example 2, the porous carbon material that has been described in Example 1 was used as an oral adsorbent and a medical adsorbent such as pharmaceuticals for internal use, which is useful for therapy and prophylaxis of diseases. Specifically, in the case where the porous carbon material that has been described in Example 1 is applied to the field of oral adsorbents or medical adsorbents, examples of the adsorbents of the present invention may include an oral adsorbent or medical adsorbent that adsorbs creatinine; an oral adsorbent or medical adsorbent that adsorbs Alizarine Cyanine Green; an oral adsorbent or medical adsorbent that adsorbs lysozyme; an oral adsorbent or medical adsorbent that adsorbs albumin; and an oral adsorbent or medical adsorbent that adsorbs organic substances having a number average molecular weight of from $1\times10^3$ to $1\times10^4$ (for example, organic molecules, or proteins); which oral adsorbents or medical adsorbents are made up with the porous carbon materials of Examples 1A to 1C. Besides, the porous carbon materials of Examples 1A to 1C can also be used as filler (absorbing agents) for blood purification columns having well-known constitutions and structures. Alternatively, a cleansing agent (cleansing agent that adsorbs fatty acids) containing the porous carbon material of any of Examples 1A to 1C was produced. This cleansing agent (cleaning agent, adsorbent for cosmetic or washing) is one which removes stain components such as sweat, oil and fat, and lipsticks, which has a skin-conditioning effect in some cases.

Example 3

Example 3 relates to a water purification adsorbent of the present invention. In Example 3, the porous carbon materials of Examples 1A to 1C are used for purification of water, or in a broad sense, for purification of fluids, for example. Or, they are able to remove active oxygen species (oxidative stress substances) such as superoxide, hydroxyl radical, hydrogen peroxide and singlet oxygen from water.

To each 40 milliliters of a test solution of Methylene blue and Black 5 dissolved or dispersed in pure water, 10 milligrams of the corresponding specimen of Examples 1A to 1C and Comparative Example 1 was added, followed by stirring at 100 rpm with a mix rotor (stirrer). Then, after stirring, the resultant mixture was filtered, and a change in absorbance of the obtained filtrate was measured. As a result, in every Examples of Examples 1A to 1C, the Methylene blue and the Black 5 were able to be absorbed better than in Comparative Example 1.

Figure 2:
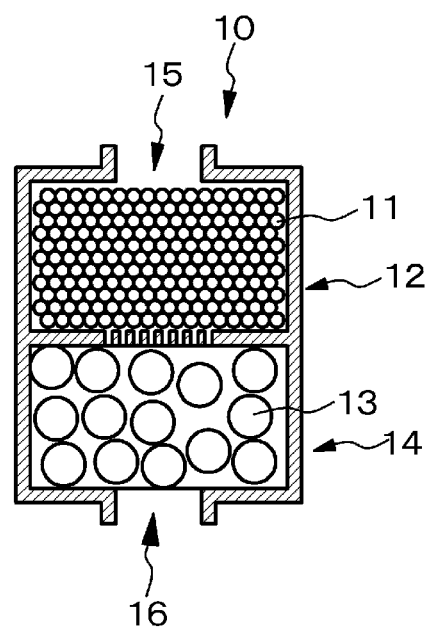
FIG. 2 is a schematic sectional view of a water cleaner of Example 3.

A sectional view of a water cleaner of Example 3 is shown in FIG. 2. The water cleaner of Example 3 is a continuous water cleaner and a faucet-coupled water cleaner where a water cleaner body is directly attached to a tip part of a water faucet. The water cleaner of Example 3 includes a water cleaner body 10, a first packing part 12 that is disposed inside the water cleaner body 10 and in which a porous carbon material 11 of any of Examples 1A to 1C is packed, and a second packing part 14 in which a cotton 13 is packed. Tap water discharged from a water faucet passes from an inlet 15 disposed to the water cleaner body 10 through a porous carbon material 11 and cotton 13 and is discharged from an outlet 16 disposed to the water cleaner body 10.

Or, as a schematic partial sectional view is shown in (A) of FIG. 3, a porous carbon material of any of Examples 1A to 1C may be assembled in a bottle (so-called PET bottle) 20 with a cap member 30. Specifically, inside the cap member 30, the porous carbon material (filter medium 40) of any of Examples 1A to 1C may be disposed and filters 31 and 32 may be disposed on a liquid inlet side and a liquid outlet side of the cap member 30 to prevent the filter medium 40 from eluting off. Then, when a liquid or water (drinkable water, a lotion, or the like) 21 in the bottle 20 is drunk or used by passing through the filter medium 40 disposed inside the cap member 30, for example, the liquid (water) can be purified, or washed. The cap member 30 is usually closed with a cap (not shown).

Or, as a schematic sectional view is shown in (B) of FIG. 3, a form in which the porous carbon material (filter medium 40) of any of Examples 1A to 1C is housed in a permeable bag 50 and the bag 50 is put into a liquid or water (drinkable water, a lotion, or the like) 21 in a bottle 20 can be adopted. A reference numeral 22 denotes a cap for closing an opening of the bottle 20.

Example 4

Example 4 relates to a carrier for carrying pharmaceuticals and a sustained release pharmaceutical of the present invention. In Example 4, based on the porous carbon materials of Examples 1A to 1C, the carriers and the sustained release pharmaceuticals including these porous carbon materials were produced. In order to allow a pharmaceutical to act effectively in the human body, it is desirable that the pharmaceutical of an appropriate amount be allowed to act for an appropriate time. Therefore, it is desirable to use a carrier capable of appropriately controlling the drug release rate. If the pharmaceutical is adsorbed to such a carrier, it is made possible to continuously release a certain amount of the pharmaceutical. Examples of uses of such a pharmaceutical/carrier composite include transdermal drugs having percutaneous absorption localized action to deliver the pharmaceutical through the skin; and oral pharmaceuticals. Specifically, after 0.01 grams of the porous carbon material of Examples 1A to 1C were subjected to impregnation overnight in a solution of 0.10-gram ibuprofen/10-milliliter hexane, the resultant mixtures were filtered through membrane filters, followed by vacuum drying at 40° C. to obtain the carriers and the sustained release pharmaceuticals.

Example 5

Example 5 relates to a cell culture scaffold (cell culture material) of the present invention. In the cell culture scaffold of Example 5, for example, by mixing a powdered product of polylactic acid, casein, glucose or the like with the porous carbon material of Examples 1A to 1C, and molding, a sheet-like cell culture scaffold made up with a thin film having a thickness of 0.5 mm was obtained. By allowing proteins or the like, which may serve as growth factors for cells, to be adsorbed to the porous carbon material and be slowly released therefrom, the culture of the cells on the cell culture scaffold was able to be carried out easily and surely. Specifically, by allowing cell growth factors necessary for cell culture scaffolds (for example, epidermal growth factor, insulin-like growth factor, transforming growth factor, nerve growth factor, etc.) to be adsorbed to the porous carbon material and be slowly released therefrom, various cells were able to be cultured efficiently.

Example 6

Example 6 relates to a carbon/polymer composite and an adsorbent sheet of the present invention. In Example 6, the porous carbon materials of Examples 1A to 1C were applied to an adsorbent for an anti-pollinosis mask, to a carbon/polymer composite and to an adsorbent sheet. A schematic diagram of the anti-pollinosis mask is shown in (A) of FIG. 4 and a diagram showing a schematic sectional structure of a main portion (adsorbent sheet) of the anti-pollinosis mask is shown in (B) of FIG. 4. The main portion of the anti-pollinosis mask has a structure in which the porous carbon material which has been made sheet-like is sandwiched between a nonwoven fabric 1, which is made of cellulose, and another nonwoven fabric 1. In order to make the porous carbon materials of Examples 1A to 1C sheet-like, a method of forming a carbon/polymer composite 1 using carboxymethyl nitrocellulose as a binder may be employed, for example. Besides, the adsorbent sheet of Example 6 is made up with a sheet member made of the porous carbon materials of Examples 1A to 1C (specifically, the carbon/polymer composite 1 using carboxymethyl nitrocellulose as a binder), and with a support member to support the sheet member (specifically, a nonwoven fabric 2 which is a support member to be sandwiching the sheet member). It can be believed that by applying the porous carbon material in the present invention to the adsorbents for various masks such as anti-pollinosis masks, for example, it enables effective adsorption of pollens by allowing protein sites of pollens to be adsorbed on the porous carbon material.

Example 7

Example 7 relates to a functional food of the present invention. In Example 7, based on the porous carbon materials of Examples 1A to 1C, the functional food including these porous carbon materials was produced. Specifically, the functional food was produced based on a method of mixing the porous carbon material, microcrystalline cellulose preparations in which sodium carboxymethyl cellulose has been coated onto microcrystalline cellulose, a sweetener and seasonings; dispersing the resultant mixture into water; kneading; and molding (shaping).

Example 8

Example 8 is a modification of Example 1 and relates to a porous carbon material composite in which a functional material has been attached to the porous carbon material described in Example 1. This porous carbon material composite is used to make up a cosmetic or a water purification adsorbent, for example. Specifically, in Example 8, based on the porous carbon materials of Examples 1A to 1C, the porous carbon material composite in which a functional material such as a metallic material having an active oxygen removal effect and a photocatalyst material has been attached to these porous carbon materials was produced.

In such porous carbon material composites, photocatalyst materials are able to be attached to the porous carbon material extremely effectively by sizes and arrangement of the fine pores, and hence, decomposition by photocatalytic activity is allowed to occur effectively. In the cosmetics, metallic materials having an active oxygen removal effect are able to be attached to the porous carbon material extremely effectively by such sizes and arrangement of the fine pores. Hence, for example, it becomes no longer necessary to use a protective colloid agent in order to form nano-size particles of platinum into a colloid; and the cosmetics are able to exhibit a high antioxidant activity against active oxygen species such as superoxide, hydroxyl radical, hydrogen peroxide and singlet oxygen which are considered to be a factor for acute inflammation, tissue disorders and aging. In addition, active oxygen species (oxidative stress substances) such as superoxide, hydroxyl radical, hydrogen peroxide and singlet oxygen can be removed from water.

The functional material may be attached to the porous carbon material after obtaining the porous carbon material. In addition, before attaching the functional material to the porous carbon material, the porous carbon material may be subjected to an activation treatment. Examples of the functional material are platinum (Pt) or a combination of platinum (Pt) and palladium (Pd). The functional material can be attached to the porous carbon material as fine particles or a thin film, for example. Specifically, a state in which the fine particles of the functional material are attached to the surface (including within pores) of the porous carbon material, the functional material in a thin film state is attached to the surface of the porous carbon material, and a state attached in sea-island form (if the surface of the porous carbon is the "sea", the functional material corresponds to the "island") can be mentioned. The term "attach" refers to a phenomenon in which different materials are adhered. Examples of methods for allowing the functional material to be attached to the porous carbon material include a method in which the porous carbon material is immersed into the solution containing the functional material to precipitate the functional material onto the surface of the porous carbon material; a method in which the functional material is precipitated onto the surface of the porous carbon material by electroless plating (chemical plating) or a chemical reduction reaction; a method in which the porous carbon material is immersed into a solution containing the precursor of the functional material, and by a heat treatment the functional material is precipitated onto the surface of the porous carbon material; a method in which the porous carbon material is immersed into a solution containing the precursor of the functional material, and by an ultrasonic irradiation treatment the functional material is precipitated onto the surface of the porous carbon material; and a method in which the porous carbon material is immersed into a solution containing the precursor of the functional material, and by making a sol-gel reaction the functional material is precipitated onto the surface of the porous carbon material.

In Example 8, a metallic material (specifically, fine particles of platinum or platinum nanoparticles) being attached to a porous carbon material was used as a functional material. More specifically, in Example 8, to 182 milliliters of diluted water, 8 milliliters of 5-millimole $H_2PtCl_6$ aqueous solution and 3.5 milligrams of L-ascorbic acid (surface protecting agent) were added, followed by stirring for a while. Subsequently, 0.43 grams of the porous carbon material described in Examples 1A to 1C was added to the resulting mixture, and then after an ultrasonic irradiation for 20 minutes, 10 milliliters of 40-millimole $NaBH_4$ aqueous solution was added thereto, followed by stirring for 3 hours. After that, by filtering with suction and drying at 120° C., a porous carbon material composite or a cosmetic (porous carbon material composite) of Example 8, which is a black powder sample, was obtained.

In the above, the present invention was described based on preferred examples. However, the present invention is not limited to these examples and can be variously modified. Regarding the porous carbon material of the present invention, suitable ranges of values of a specific surface area based on a nitrogen BET method and of pore diameters were described. However, the description is not intended to completely deny the possibility that the value of the specific surface area and the value of the pore diameters may be outside the range mentioned above. That is, the above-described suitable ranges are only intended to be particularly preferred ranges in obtaining the effects of the present invention. As long as the effects of the present invention are able to be obtained, the values such as the specific surface area may have some minor deviations from the above-described ranges.

DESCRIPTION OF REFERENCE NUMERALS 1 carbon/polymer composite
2 nonwoven fabric
10 water cleaner body
11 porous carbon material
12 first packing part
13 cotton
14 second packing part
15 inlet
16 outlet
20 bottle
21 liquid or water
22 cap
30 cap member
31, 32 filter
40 filter medium
50 bag

The invention claimed is:

1. A porous carbon material that:
   includes peat as a raw material, wherein the porous carbon material is heated at a predefined temperature that is selected based on specifications of the peat; and
   the heated porous carbon material has a total of volume of fine pores having a diameter of from $1\times10^{-8}$ m to $2\times10^{-7}$ m, obtained by a non-localized density functional theory method, of 0.5 cm$^3$/g or more,
   wherein the heated porous carbon material has at least one peak in a range of 3 nm to 20 nm and has a pore diameter distribution, obtained by a non-localized density functional theory method, in which a ratio of a total of volume of fine pores having pore diameters in the range of 3 nm to 20 nm, with respect to a sum total of volume of all fine pores, is 0.28 or more,
   wherein the sum total of volume of all fine pores is in the range of 1.078 cm$^3$/g to 1.52 cm$^3$/g, and
   wherein the heated porous carbon material adsorbs molecules having a number average molecular weight in the range of about $1\times10^2$ to about $1\times10^6$, and wherein the heated porous carbon material comprises macropores having a pore diameter greater than 50 nm.

2. The porous carbon material of claim 1, wherein the heated porous carbon material is included in an adsorbent.

3. The porous carbon material according to claim 2, wherein the adsorbent adsorbs molecules having a number average molecular weight in the range of about $1\times10^3$ to about $1\times10^6$.

4. The porous carbon material of claim 1, wherein the heated porous carbon material is included in an adsorbent that adsorbs α-amylase.

5. The porous carbon material of claim 1, wherein the heated porous carbon material is included in an adsorbent that adsorbs lysozyme.

6. The porous carbon material of claim 1, wherein the heated porous carbon material is included in an adsorbent for a cigarette filter that adsorbs benzopyrene.

7. The porous carbon material of claim 1, wherein the heated porous carbon material is included in an oral adsorbent.

8. The porous carbon material of claim 1, wherein the heated porous carbon material is included in a medical adsorbent.

9. The porous carbon material of claim 1, wherein the heated porous carbon material is included in a filler for a blood purification column.

10. The porous carbon material of claim 1, wherein the heated porous carbon material is included in a water purification adsorbent.

11. The porous carbon material of claim 1, wherein the heated porous carbon material is included in a cleansing agent that adsorbs fatty acids.

12. The porous carbon material of claim 1, wherein the heated porous carbon material is included in a carrier for carrying a pharmaceutical.

13. The porous carbon material of claim 1, wherein the heated porous carbon material is included in a sustained release pharmaceutical.

14. The porous carbon material of claim 1, wherein the heated porous carbon material is included in a cell culture scaffold.

15. The porous carbon material of claim 1, wherein the heated porous carbon material is included in an adsorbent for a mask.

16. The porous carbon material of claim 1, wherein the heated porous carbon material is included in a carbon/polymer composite, the carbon/polymer composite including a binder.

17. The porous carbon material of claim 1, wherein the heated porous carbon material is included in a sheet member of an adsorbent sheet, the adsorbent sheet including a support member to support the sheet member.

18. The porous carbon material of claim 1, wherein the heated porous carbon material is included in a functional food.

19. The porous carbon material of claim 1, wherein the heated porous carbon material comprises micropores having a pore diameter smaller than 2 nm.

20. The porous carbon material of claim 1, wherein the heated porous carbon material has a specific surface area of 836 $m^2/g$ or more.

* * * * *